United States Patent
Ghidoni et al.

(10) Patent No.: US 9,925,160 B1
(45) Date of Patent: Mar. 27, 2018

(54) METHODS FOR TREATING CARDIAC REPERFUSION INJURY

(71) Applicants: Universita' Degli Studi di Milano, Milan (IT); Policlinico Sandonato, San Donato Mllanese (IT)

(72) Inventors: Riccardo Ghidoni, Milan (IT); Paola Signorelli, Legnano (IT); Luigi Anastasia, Milan (IT)

(73) Assignees: UNIVERSITA' DEGLI STUDI DI MILANO, Milan (IT); POLICLINICO SAN DONATO S.P.A., San Donato Milanese (IT)

( * ) Notice: Subject to any disclaimer, the term of this patent is extended or adjusted under 35 U.S.C. 154(b) by 0 days.

(21) Appl. No.: 15/406,930

(22) Filed: Jan. 16, 2017

(51) Int. Cl.
*A61K 31/198* (2006.01)
*A61K 47/48* (2006.01)
*A61K 9/107* (2006.01)
*A61K 9/00* (2006.01)

(52) U.S. Cl.
CPC .......... *A61K 31/198* (2013.01); *A61K 9/0019* (2013.01); *A61K 9/107* (2013.01); *A61K 47/48046* (2013.01)

(58) Field of Classification Search
CPC .................................................. A61K 31/198
See application file for complete search history.

(56) References Cited

PUBLICATIONS

Reforgiato et al. Basic Res. Cardiol (2016) 111-12).*
Yellon D.M., et al., "Myocardial reperfusion injury", N Engl J. Med 357;11, 2007 1121-1135.
Zhang, Dx, et al., Production and metabolism of ceramide in normal and ischemic-reperfused myocardium of rats, Basic Res Cardiol. 96:267-274 (2001).
Zhao Z-Q., et al., "Inhibition of myocardial injury by ischemic postconditioning during reperfusion: comparison with schemic preconditioning", Am j Physiol Heart Cir Physiol 285 H579-H588, 2003.
Reforgiato M.R., et al., "Inhibition of ceramide de novo synthesis as a postischemic strategy to reduce myocardial reperfusion injury", Basic Res Cardiol (2016) 111:12.
Airola MV, et al., "Sphingolipid metabolism and neutral sphingomyelinases", Handb Exp Pharmacol. 2013 ; (2015): 57-76.
Argaud L, et al., "Postconditioning inhibits mitochondrial permeability transition", Circulation 2005; 111:194-197.
Balogun E., et al., "Curcumin activates the heam oxygenase-1 via regulation of Nrf2 and the antioxidant-responsive element", Biochem J (2003) 371, 887-895.
Bartke N., et al., "Bioactive sphingolipids: metabolism and function", J. Lipid Res. 2009 50: S91-S96.
Calvert, JW, et al., "Hydrogen sulfide mediates cardioprotection through Nrf2 signaling", Circ Res Aug. 14, 2009; 105(4): 365-374.
Caretti A., et al., "Anti-inflammatory action of lipid nanocarrier-delivered Myriocin: therapeutic potential in cystic fibrosis", Biochim Biophys Acta. Jan. 2014; 1840(1): 586-594.
Chun L., et al., "Inhibition of ceramide synthesis reverses endothelial dysfunction and atherosclerosis in streptozotocin-induced diabetic rats", Diabetes Research and Clinical Practice 93 (2011) 77-85.
Collard C.D., et al., "Pathophysiology, clinical manifestations and prevention of ischemia-reperfusion injury", Anesthesiology 2001; 94:1133-8.
Cordis G.A., et al., "HPTLC analysis of sphingomylein, ceramide and sphingosine in ischemic/reperfused rat heart", Journal of Pharmaceutical and Biomedical Analysis, 16 (1998) 1189-1193.
Cui J., et al., "Role of ceramide in ischemic preconditioning", J Am Coll Surg 2004; 1978:770-777.
Cuzzocrea S., et al., "Anti-inflammatory and anti-apoptotic effects of fumosin B1, an inhibitor of ceramide synthase, in a rodent model of splanchnic ischemia and reperfusion injury", TJPET 327: 45-57, 2008.
Darling C.E., et al, "Postconditioning via stuttering reperfusion limits myocardial infarct size in rabbit hearts: role of ERK1/2", Am J Physiol Heart Circ Physiol 289: H1618-H1626 2005.
Dittoe N., et al., "Quantitative left ventricular systolic function: from chamber to myocardium", Crit Care Med 2007; 35[Suppl.]:S330-S339.
Drevinge C., et al., "Cholesteryl esters accumulate in the heart in a porcine model of ischemia and reperfusion" PLOSONE Apr. 2013 vol. 8, issue 4 e61942.
Empinado HM, et al., "Diaphragm dysfunction in heart failure is accompanied by increases in neutral sphingomyelinase activity and ceramide content", Eur J Heart Fail. May 2014; 16(5): 519-525.
Escriva' L., et al., "In vivo toxicity studies of fusarium mycotoxins in the last decade: a review", Food and Chemical Toxicology 78 (2015) 185-206.
Gomez L., et al., "A novel role for mitochondrial sphingosine-1-phosphate produced by sphingosine kinase-2 in PTP-mediated cell survival during cardioprotection", Basic Res Cardiol. Nov. 2011; 106(6): 1341-1353.
Gulbins, E. et al., "Raft ceramide in molecular medicine", Oncogene (2003) 22, 7070-7077.
Hearn, L, et al., "Desipramine for neuropathic pain in adults", Cochrane database of Systematic Reviews, 2014 Issue 9.
Herskowitz, A., et al., "Cytokine mRNA expression in postischemic/reperfused myocardium", Am J Pathol 1995, 146:419-428.
Heusch G., "Molecular basis of cardioprotection signal transduction in ischemic pre-, post-, and remote conditioning", Circ. Res. 2-15; 116; 674-699.
Heusch G., "Cardioprotection: chances and challenges of its translation to the clinic", Lancet 2013; 381: 166-75.
Hodson A.E., et al., "Insulin treatment increases myocardial ceramide accumulation and disrupts cardiometabolic function", Cardiovasc Diabetol (2015) 14:153.

(Continued)

*Primary Examiner* — Shirley V Gembeh
(74) *Attorney, Agent, or Firm* — Silvia Salvadori, P.C.; Silvia Salvadori

(57) ABSTRACT

The inventors have made the surprising discovery that when ceramide production is upregulated in the infarct and at-risk areas upon reperfusion injury in the heart, such upregulation is effected through the de novo ceramide synthesis pathway. Upon treatment of cardiac tissues subject to reperfusion injury with a specific inhibitor of the novo ceramide synthesis pathway (myriocin), the inventors have determined that the inhibition of such pathway not only reduces the inflammation of the interested area, but most surprisingly reduces infarct size, ameliorates cardiac contractility and activates cell detoxification and survival programs. There is thus provided an inhibitor of de novo ceramide synthesis pathway, particularly myriocin, for the treatment of cardiac reperfusion injury.

4 Claims, 14 Drawing Sheets

(56) References Cited

PUBLICATIONS

Hua W., et al., Cardioprotection of H2S by downregulating iNOS and upregulating HO-1 expression in mice with CVB3-induced myocarditis, Live Sciences 93 (2013) 949-954.

Ibanez B., et al., "Evolving Therapies for Myocardial Ischemia/Reperfusion Injury", JACC vol. 65, No. 14, 2015: 1454-71.

Jaswal, JS, et al., "Targeting fatty acid and carbohydrate oxidation-A novel therapeutic intervention in the ischemic and failing heart", Biochimica et Biophysica Acta 1813 (2011) 1333-1350.

Kleinbongard P., et al., "Extracellular signalling molecules in the ischaemic/reperfused heart-druggable and translatable for cardioprotection?" British Journal of Pharmacology (2015) 172 2010-2025.

Kornhuber J, et al., "Functional inhibitors of acid sphingomyelinase (FIASMAs): a novel pharmacologica group of drugs with broad clinical applications", Cell Physiol Biochem 2010;26:09-20.

Lang, R.M., et al., "Recommendations for chamber quantification", Eur J Echocardiography (2006) 7, 79-108.

Lee T-M., et al., "Antiarrhythmic effect of lithium in rats after myocardial infarction by activation of Nrf2/HO-signaling", Free Radical Biology and Medicine 77 (2014) 71-81.

Longborg, J.T., "Targeting reperfusion injury in the era of primary percutaneous coronary intervention: hope or hype?", Heart, 2015; 101:1612-1618.

Medler, T.R., et al., "Apoptotic sphingolipid signaling by ceramides in lung endothelial cells", Am J. Respir Cell Mol Biol vol. 38, pp. 639-646, 2008.

Messaoudi S.E., et al., "Impact of metformin on endothelial ischemia-reperfusion injury in humans in vivo: a prospective randomized open, blinded-endpoint study", PLOS ONE, Apr. 2014, vol. 9, issue 4, 1-7.

Mezzaroma, E., et al., "The inflammasome promotes adverse cardiac remodeling following acute myocardial infarction in the mouse", PNAS, Dec. 6, 2011, vol. 108, No. 49 pp. 19725-19730.

Munoz-Olaya J.M., et al., "Synthesis and biological activtiy of a novel inhibitor of dihydroceramide desaturase", ChemMedChem 2008, 3, 946-953.

Opfermann P., et al., "A pilot study on reparixin, a CXCR1/2 antagonist, to assess safety and efficacy in attenuating ischaemia-reperfusion injury and inflammation after on-pump coronary artery by pass graft surgery", Clinical and Experimental Immunology 2014, 180; 131-142.

Ovize M., et al., "Myocardial conditioning, opportunities for clinical translation", Circ Res 2013:113:439-450.

Park T-S, et al., "Ceramide is a cardiotoxin in lipotoxic cardiomyopathy", J. Lipid Res. 2008.49:2101-2112.

Pei XM., et al., "S100A8 and S100A9 are associated with doxorubicin-induced cardiotoxicity in the heart of diabetic mice", Frontiers in Physiology Aug. 2016, vol. 7 pp. 1-14.

Romson J.L., et al., "Reduction of the extent of ischemic myocardial injury by neutrophil depletion in dog", Circulation 67 No. 5, 1983: 1016-1023.

Schwartz L.M., et al., "Ischemic postconditioning during reperfusion activates Akt and ERK without protecting against lethal myocardial ischemia-reperfusion injury in pigs", Am J Physiol Heart Cir Physiol 290: H1011-H1018, 2006.

Siow D., et al., "ORMDL/serine palmitoyltransferase stoichiometry determines effects of ORMDL3 expression on sphingolipid biosynthesis", J. Lipid Res. 2015 56:898-908.

Skyschally A., et al., "Ischemic postconditioning: experimental models and protocol algorithms", Basic Res Cardiol (2009) 104:469-483.

Strettoi E., et al., "Inhibition of ceramide biosynthesis preserves photoreceptor structure and function in a mouse model of retinitis pigmentosa", PNAS Oct. 26, 2010, vol. 107, No. 43 pp. 18706-18711.

Tang X-L, et al., "Cardioprotection by postconditioning in conscious rats is limited to coronary occlusions < 45 min", Am J Physiol Heart Circ Physiol 291: H2308-H2317, 2006.

Tsang A., et al., "Postconditioning: A form of "modified reperfusion" protects the myocardium by activating the phosphatidylinositol3-kinase-Akt pathway", Circ Res, 2004; 95:230-232.

Ussher J.R., et al., "Inhibition of serine palmitoyl transferase I reduces cardiac ceramide levels and increases glycolysis rates following diet-induced insulin resistance", PLOSONE May 2012 vol. 7, issue 5 e37703.

Usta E., et al., "The challenge to verify ceramide's role of apoptosis induction in human cardiomycocytes—a pilot study", Journal of Cardiothoracic Surgery 2011, 6:38.

Wadsorth J.M., et al., "The chemical basis of serine palmitoyltransferase inhibition by myriocin", J. Am. Chem. Soc. 2013, 135, 14276-14285.

Yang X-M, et al., "Multiple, brief coronary occlusions during early reperfusion protect rabbit hearts by targeting cell signaling pathways", J Am Coll Cardiol 2004; 44:1103-10.

* cited by examiner

METHODS FOR TREATING CARDIAC REPERFUSION INJURY

FIELD OF THE INVENTION

The present invention relates to the use of de novo ceramide synthesis pathway inhibitors, particularly myriocin, to treat cardiac reperfusion injury.

BACKGROUND OF THE INVENTION

Although necessary to recover myocardial function, reperfusion of infarcted tissue is a cause of additional injury which should be therapeutically controlled. Unfortunately, at present, the unique effective post conditioning maneuver is still impracticable in most of the patients and reperfusion-induced injury, after coronary artery occlusion and myocardial ischemia (Ischemia/reperfusion, I/R), results in increased infarct size and development of arrhythmia and contractile dysfunction [1].

Sterile inflammation is a major component of reperfusion injury. Tissue-released danger-associated molecular patterns (DAMPs) that activate cellular receptors triggering inflammasome formation [2] massive release of reactive oxygen species (ROS) and reactive nitrogen species (RNS) [3], neutrophilic infiltrates releasing damaging proteases are among the causes which concur to the progression of cardiac injury upon reoxygenation [4]. Innovative cardioprotective pharmacological interventions should essentially represent an attempt to evoke defensive and anti-apoptotic signals. At this aim, reperfusion conditioning with β-blockers, angiotensin-converting enzyme inhibitors and angiotensin II receptor antagonists, statins and antiplatelet drugs [5-8], as well as antidiabetics [9] and anti-inflammatory agents [10], have been lately applied with mixed results. However, thus far, pharmacological conditioning approaches have fallen short of equaling the efficiency of ischemic postconditioning by intermittent reperfusion/reocclusion cycles. A landmark in postischemic recovery research would be the identification of targets for pharmacological postconditioning among key activators of the noxious cascade inducing myocardial injury. This should specifically occur in the reperfused perinecrotic tissue, named area at risk.

The hypoxic or anoxic insult of the infarcted tissue typically leads to a reduction of metabolic oxidative activity in the interested area, and this is currently regarded as an important contribution to energy depletion and to the insurgence of arrhythmias [11]. Post infarct therapeutic approaches should thus not only limit inflammation and oxidative damages, but also stimulate the recovery of a suitable rate of glycolysis and/or beta-oxidation in the affected tissues.

Ceramide, a sphingolipid mediator and central hub of the sphingolipid metabolism, plays a key role as an inhibitor of proliferation and an activator of both inflammatory signaling and apoptosis [12].

Ceramide accumulation typically occurs via three pathways [13]: 1) the hydrolysis of sphingomyelin by sphingomyelinases (SMases), 2) the de novo pathway, which uses serine and palmitoyl-CoA as initial substrates to generate ceramide through the subsequent action of four classes of enzymes: a serine palmitoyl transferases (SPT), a 3-ketodihydrosphingosine reductase, a dihydroceramide synthases, and a dihydroceramide desaturase, and 3) the salvage pathway, whereby complex sphingolipids are cleaved to release the sphingosine backbone, which can be re-acylated to produce ceramide. The contribution of each of these pathways in ceramide accumulation and induced signaling is profoundly different, due to i) the topology of ceramide formation and interaction with signaling proteins, ii) the amount of ceramide formed and the presence of different ceramide-consuming enzymes such as sphingomyelin synthases or ceramidases, or glycosyl ceramide transferases. Thus, depending on the pathway involved, ceramide signaling can be transient or sustained, or can induce a variety of different effects such as differentiation or apoptosis.

External stimuli and activated receptors can unleash sphingomyelinases thereby regulating membrane lipids raft formation and related signaling pathways [14]. The de novo synthesis, occurring under cell stress conditions, also promotes secondary sphingomyelinase activation [15], which may further amplify stress signals and a ungoverned inflammatory response, suggesting that ceramide accumulates in a self-amplifying mechanism when its de novo synthesis is enhanced under pathological conditions.

Ceramide degradation releases the sphingolipid backbone, which can be further degraded or phosphorylated to form sphingosine-1-phosphate (SIP). SIP antagonizes ceramide, as it exerts pro-survival and antiinflammatory actions. Ceramide and SIP have been described as rheostats, as variations of their relative concentration can drive cell fate in opposite directions [48]. SIP signaling was proved to reduce I/R injury, linking myocardial damage to sphingolipid metabolism [16]. A number of evidences suggest that ceramide is involved in the mechanism of myocardial injury. Myocardial activities of sphingolipid metabolism enzymes were found to be modulated after I/R [17]. Reperfusion after ischemia induces ceramide accumulation in the myocardium [17]. while lowering sphingomyelin [18]. On the other hand, the ischemic preconditioning cardioprotection significantly reduces subsequent reperfusion-induced ceramide increase [19]. Noteworthy, in a recent study on a porcine model of I/R, the separate analysis of the infarct area, characterized by irreversible injury, from the reversibly injured area at risk, detected a selective ceramide increase in the latter [20]. Neutral sphingomyelinase activation was reported in infarcted myocardium [21]. Furthermore, a study on cardiac biopsies from the right auricle treated in vitro showed that inhibition of acid sphingomyelinase activity by desipramine, which indirectly inhibits acid sphingomyelinase activity [22], protected from apoptosis after cardioplegia and reperfusion [23]. In vivo reperfusion with desipramine also conferred partial cardioprotection against I/R [19]. In a model of intestinal I/R injury, ceramide synthesis inhibition by fumonisin B1 reduced oxidative stress and inflammation damage [24].

Desipramine has a broad spectrum of action being a tricyclic antidepressant drug and cannot be considered a specific inhibitor of merely ceramide release [25], fumonisin B1 has a known high toxicity [26] and these considerations limit the application of both drugs.

De novo synthesis of ceramide was implicated in cardiac toxicity and both genetic and pharmacological inhibition of serine palmitoyl transferase (SPT), the first and rate-limiting enzyme in the biosynthesis pathway, improved systolic function and prolonged survival in a murine model of cardiomyopathy [27].

Myriocin ((2S,3R,4R,6E)-2-Amino-3,4-dihydroxy-2-(hydroxymethyl)-14-oxo-6-eicosenoic acid) is a specific SPT inhibitor [28].

It was previously demonstrated that nanocarriers (solid lipid nanocarriers, SLN) loaded with the ceramide synthesis inhibitor myriocin are effective in reducing apoptosis in two different models of proteinophaty-induced oxidative stress and degeneration: retinal photoreceptor loss in Retinitis Pigmentosa [29] and chronic pulmonary inflammation in Cystic Fibrosis [30]. It is also known that the administration of myriocin may be beneficial to heart and circulation conditions associated to glucose metabolism defects of diabetes [31-33].

SUMMARY OF THE INVENTION

The inventors have made the surprising discovery that when ceramide synthesis de novo production is increased in the infarct and at-risk areas upon reperfusion injury in the heart, such increase is effected through the de novo ceramide synthesis pathway, by both enzyme enhanced transcription and activation mechanisms. Upon treatment of cardiac tissues subject to reperfusion injury with a specific inhibitor of the de novo ceramide synthesis pathway (myriocin), the inventors have determined that the inhibition of such pathway not only reduces the inflammation of the interested area, but, most surprisingly, reduces infarct size upon the reperfusion maneuver, thus ameliorating cardiac contractility after the infarct and, most importantly, it activates cell detoxification and survival programs in the risk area thus favoring its recovery, without affecting the healthy tissues.

Provided herein is hence a method to treat cardiac reperfusion injury in a mammal, comprising administering to such mammal a composition comprising an inhibitor of the de novo ceramide synthesis pathway, or a prodrug thereof.

DETAILED DESCRIPTION OF THE INVENTION

Figure 1:
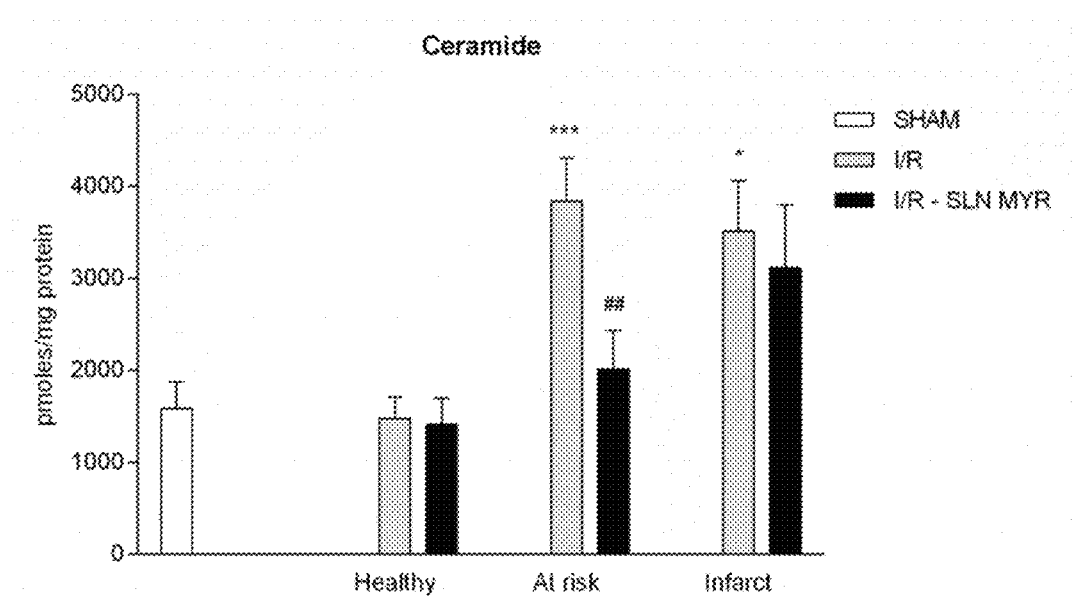
FIG. 1 portrays the ceramide levels in sham and in the healthy, at risk and infracted areas of I/R and SLN-myriocin treated hearts.

As stated above, there is provided method to treat cardiac reperfusion injury in a mammal, comprising administering to such mammal a composition comprising an inhibitor of the de novo ceramide synthesis pathway, or a prodrug thereof.

In some embodiments, the mammal is selected from the lists of human, dog, cat, bovine, horse and avian.

In some embodiments, the inhibitor of the de novo ceramide synthesis pathway is selected from the list of a serine palmitoyl transferase inhibitor, a 3-ketodihydrosphingosine reductase inhibitor, a dihydroceramide synthase inhibitor, a dihydroceramide desaturase inhibitor and prodrugs thereof.

In specific embodiments, the serine palmitoyl transferase inhibitor is myriocin, stereoisomers, or mixtures of stereoisomers thereof and their pharmaceutically acceptable salts or prodrugs.

In some embodiments, the inhibitor is conjugated to a drug carrier. In particular embodiments, such drug carrier is a nanocarrier. In more specific embodiments such nanocarrier is a lipidic nanocarrier.

Definitions

As used herein, "drug carrier" means an entity which, when administered in the form of a drug carrier-drug conjugate, enhances the performance of such drug, for example and not limitedly by increasing the delivery of the drug to a target tissue, the effectiveness, selectivity and/or safety of the drug.

As used herein, "drug carrier-inhibitor conjugate" means the physical entity formed by the drug carrier and the inhibitor through non-covalent bonding the two, e.g. by encapsulation or adsoption.

As used herein, a "nanocarrier" is a nanoscopic drug carrier, which can be rationally designed.

As used herein, a "prodrug" means a chemical derivative of a drug which is transformed in vivo to yield such drug into its active form which possesses therapeutic effect, for example and not limitedly by hydrolysis or metabolism.

The skilled may refer to textbooks in the appropriate technical field or to the scientific literature in order to find examples falling under the above definitions.

Formulation

Compositions provided herein may be in the form of tablets or lozenges formulated in a conventional manner. For example, tablets and capsules for oral administration may contain conventional excipients including, but not limited to, binding agents, fillers, lubricants, disintegrants and wetting agents. Tablets may be coated according to methods well known in the art.

Compositions provided herein may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives.

Compositions provided herein may also be formulated as suppositories, which may contain suppository bases including, but not limited to, cocoa butter or glycerides.

Compositions provided herein may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane.

Compositions provided herein may also be formulated as transdermal formulations comprising aqueous or nonaqueous vehicles including, but not limited to, creams, ointments, lotions, pastes, medicated plaster, patch, or membrane.

Compositions provided herein may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents.

Administration

Administration of the compositions using the method described herein may be orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intraarticular.

The composition may be administered at any time point prior to reperfusion including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins, 5 mins., 4 mins., 3 mins, 2 mins, and 1 mins prior to reperfusion.

The composition may be administered at any time point prior to injury including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins, 5 mins., 4 mins., 3 mins, 2 mins, and 1 mins. prior to injury.

The composition may be administered at any time point after reperfusion including about 1 min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr after reperfusion.

Dosage

The method may comprise administering a therapeutically effective amount of the composition to a patient in need thereof. The therapeutically effective amount required for use in therapy varies with the nature of the condition being treated, the length of time desired to increase hematopoietic stem cells into the bloodstream, and the age/condition of the patient. In general, however, doses employed for adult human treatment typically are in the range of 0.001 mg/kg to about 200 mg/kg per day. The dose may be about 1 µg/kg to about 100 µg/kg per day. The desired dose may be conveniently administered in a single dose, or as multiple doses administered at appropriate intervals, for example as two, three, four or more sub-doses per day. Multiple doses may be desired, or required.

The dosage may be at any dosage including, but not limited to, about 0.1 µg/kg, 0.2 µg/kg, 0.3 µg/kg, 0.4 µg/kg, 0.5 µg/kg, 0.6 µg/kg, 0.7 µg/kg, 0.8 µg/kg, 0.9 µg/kg, 1 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg or 1 mg/kg.

EXAMPLES

The invention is now described by means of non-limiting examples.

Materials and Methods

Solid Lipid Nanocarrriers (SLN)-Myriocin Preparation

Solid lipid nanocarrriers loaded with myriocin were prepared as described in [29], adjusting myriocin concentration to 2 mM. The preparation was stored at −80° C. until use. SLN-myriocin stock was diluted 1:8 in 0.9% NaCl sterile solution, avoiding vortexing and freezing, obtaining an emulsion used for intramyocardial injection.

Ethics Statement

Animal studies were conducted in accordance with the Guide for the Care and Use of Laboratory Animals (National Institutes of Health Publication, No. 85-23, revised 1996) and with the ARRIVE guidelines and adhered strictly to the Italian Ministry of Health guidelines for the use and care of experimental animals.

Left Anterior Descending (LAD) Coronary Ligature

Figure 2:
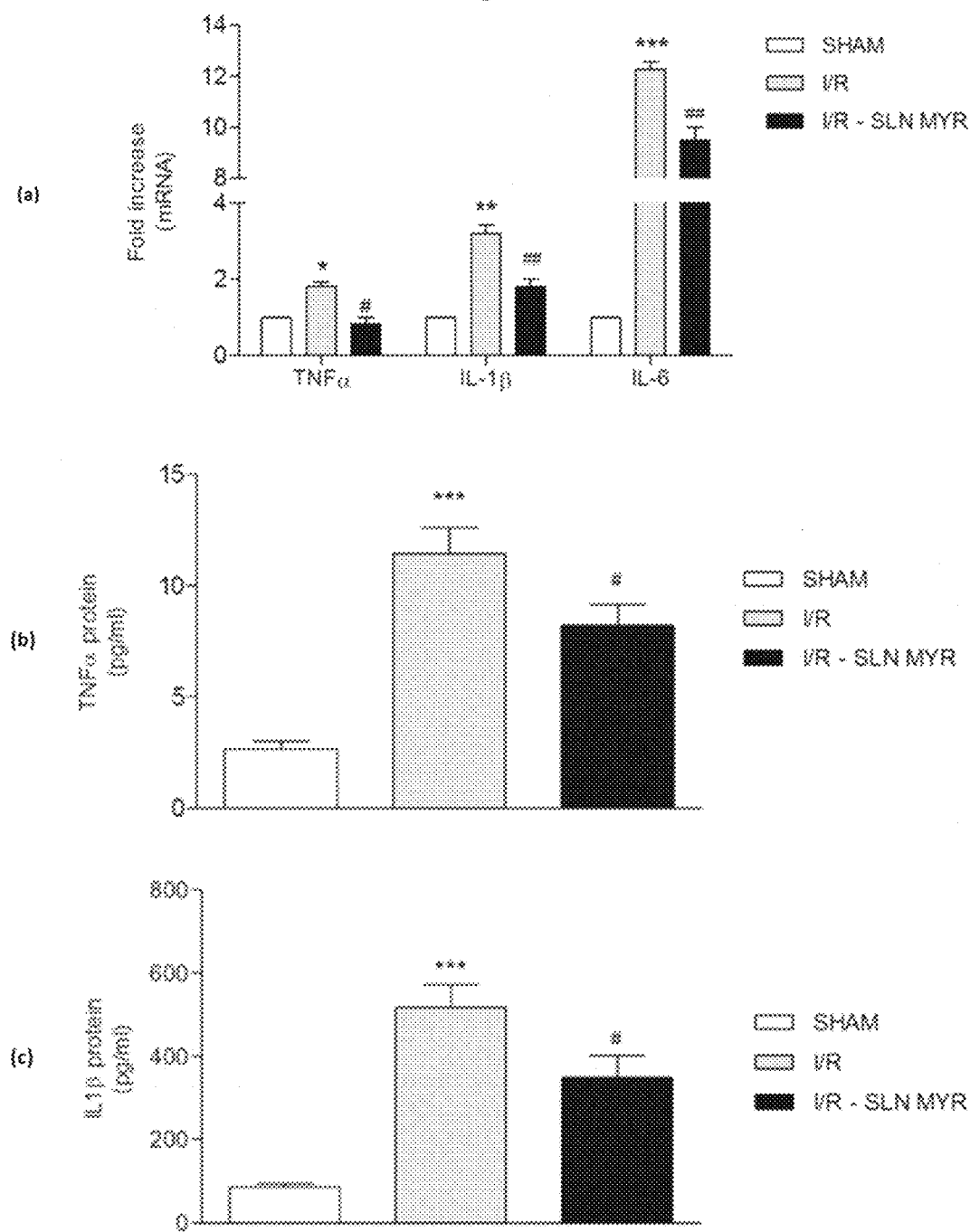
FIG. 2 shows inflammatory cytokine markers (IL1-β, TNF-α and IL6): mRNA expression levels (a); the protein level of such markers (b), (c) and (d) in control (sham) and I/R mice hearts treated or untreated with SLN-myriocin.
Figure 2:
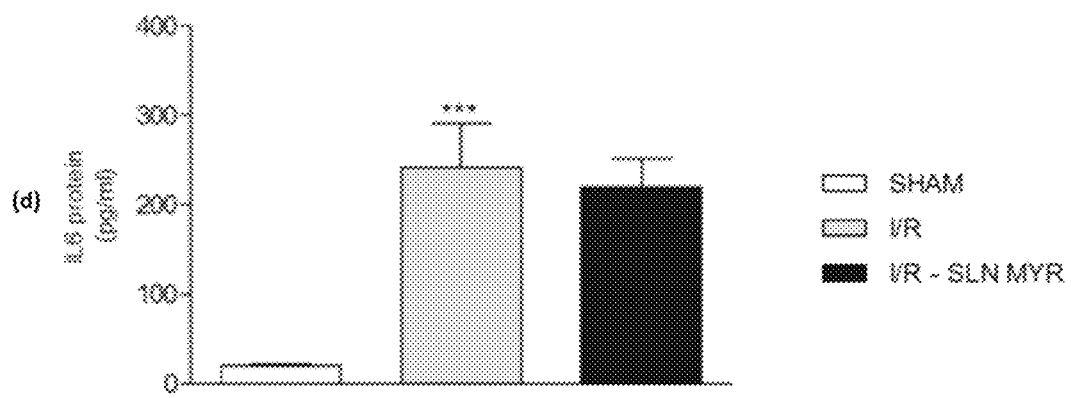

After anesthesia with 2,2,2-tribromoethanol (Avertin, Sigma-Aldrich, USA), 9 weeks old and male mice C57BL6 (Charles River Laboratories Italia, Italy) were subjected to LAD coronary occlusion. Mice were ventilated through an endotracheal tube at 200 µL of tidal volume with a respiration rate of 110 breaths/min; they were placed in a supine position on a heating pad at 37° C. to maintain a constant body temperature. Then, a thoracotomy between the second and third rib was performed and the heart exposed to insert a 6-0 propylene suture 2 mm below the tip of the left auricle. The suture was tied with two knots over the 1-mm polyethylene tube. After 30-min ischemia, coronary occlusion was released for 3 h by untying the knots and the heart reperfused. In a treated group of mice, 20 µL of SLN-myriocin was injected into the left ventricle cavity, from the heart apex, while empty SLN was used in a control group (see Supplementary FIG. 2). In a mock infarcted group of mice (sham), animals were subjected to the same surgical procedure, except that coronary ligation was omitted. At the end of reperfusion, the coronary was re-occluded, 100 µL of 4% (w/v) Evans blue was injected into the apex of the heart to identify the ischemic area by dye exclusion and the heart frozen in liquid N2 to be stored at −80° C. until analysis.

Quantitative Image Analysis on Heart Sections

To measure the infarct area and the area at risk, each heart was cut into 1-mm thick slices, perpendicularly to the apex to base axis and parallel to the transverse plane, cutting the left ventricle, interventricular septum and right ventricle. After three 1-min washes in 0.9% (w/v) NaCl, the slices were incubated in 1% triphenyl tetrazolium chloride (TTC) (Sigma-Aldrich, USA) in sodium phosphate buffer for 5 min to counterstain surviving cells in the area at risk. The extent of stained and unstained areas was calculated for each slice from digital images using IPLab Scientific Image Processing software. The area at risk was expressed as the percentage of total area (i.e., the entire section's surface), whereas the infarct area was expressed as the percentage of the area at risk. Percentages were calculated as the mean across all sections of one heart. At the completion of this imaging procedure, samples were processed for additional biochemical analyses.

Ceramide Quantitation

The healthy, at-risk and infarcted areas were separated by dissection, weighed and homogenized in phosphate saline buffer (PBS) containing protease inhibitor (Sigma-Aldrich, by using a tissue grinder and a disperser-homogenizer. The content in distinct ceramide species was analyzed by liquid chromatography-mass spectrometry (LCMS). Shortly, sphingolipid extracts were prepared by Bligh-Dyer method, fortified with internal standards [Ndodecanoyl-sphingosine, N-dodecanoyl-glucosyl-sphingosine, N-dodecanoyl-sphingosyl-phosphorylcholine, C17 sphinganine (0.2 nmol each) and C17 sphinganine-1phosphate (0.1 nmol)] and analyzed as reported [34]. The ceramide content was normalized by total protein content expressed in milligram.

qRT-PCR

Total RNA was extracted from the myocardial risk area dissected tissue using smarter nucleic acid sample preparation (Stratec Molecular, Germany) according to the manufacturer's instructions and stored at −80° C. Purified RNA was quantified by Quanti-iT™ RNA Assay kit (Invitrogen Life Technologies Italia, Italy), 11 g was reverse transcribed with MMLV reverse transcriptase (Promega Italia, Italy), and the thus-obtained cDNA was stored at −20° C. The amplification of target genes was performed using Sybr Premix Ex Taq (Tli RNaseH Plus) (Takara, USA), ROX as reference dye and StepOnePlus™ instrument (Applied Biosystem Life Technologies Italia, Italy) Amplified genes included serine palmitoyltransferase, long chain base subunit 1 (SPTLC1), serine palmitoyltransferase long chain base subunit 2 (SPTLC2), tumor necrosis factora (TNF-α), interleukin-1b (IL-1β), interleukin-6 (IL-6), heme oxygenase 1 (HO1) and glyceraldehyde-3-phosphate dehydrogenase (GAPDH) as detailed in the table below

| GENE | SEQUENCE 5' à 3' |
| --- | --- |
| Sptlc 1 (Serine palmitoyl transferase long chain base subunit 1) | Fw AGTGGTGGGAGAGTCCCTTT (SEQ ID NO: 1) Rv CAGTGACCACAACCCTGATG (SEQ ID NO: 2) |
| Sptlc 2 (Serine palmitoyl transferase long chain base subunit 2) | Fw CCTGTCAGCAGCTCATACCA (SEQ ID NO: 3) Rv CACACTGTCCTGGGAGGAAT (SEQ ID NO: 4) |
| Tnf-α (Tumor necrosis factor α) | Fw CCACCACGCTCTTCTGTCTA (SEQ ID NO: 5) Rv CTGATGAGAGGGAGGCCATT (SEQ ID NO: 6) |
| Il1-β (Interleukin 1 β) | Fw AAGAAGAGCCCATCCTCTGT (SEQ ID NO: 7) Rv CTAATGGGAACGTCACACACC (SEQ ID NO: 8) |
| IL-6 (Interleukin 6) | Fw TGTTCTCTGGGAAATCGTGGA (SEQ ID NO: 9) Rv TGCAAGTGCATCATCGTTGT (SEQ ID NO: 10) |
| HO-1 (Heme oxygenase 1) | Fw TCTATCGTGCTCGCATGAAC (SEQ ID NO: 11) Rv CTGTCTGTGAGGGACTCTGG (SEQ ID NO: 12) |
| Gapdh (Glyceraldehyde 3-phosphate dehydrogenase) | Fw AACTTTGGCATTGTGGAAGG (SEQ ID NO: 13) Rv ACACATTGGGGGTAGGAACA (SEQ ID NO: 14) |

Relative mRNA expression of target genes was normalized to the endogenous GAPDH control gene and represented as fold change versus control, calculating $2^{-\Delta\Delta Ct}$ Redox Imbalance Analysis To determine the level of oxidative stress in the tissue homogenates from the area at risk, we measured the capacity of in vivo formed hydroperoxides (ROMs) to generate in vitro alkoxyl (R—O*) and peroxyl (R—OO*) radicals in the presence of iron released from plasma by an acidic buffer by the d-ROMS test (DIACRON Labs S.r.l., Grosseto, Italy). The test results are expressed in mmol/L of $H_2O_2$. The analytical procedure described for human samples in endpoint mode was adapted for determination in mice homogenates. Water, calibrator (7.53 mM in $H_2O_2$ equivalents) or plasma samples (1 pt) were added into the wells of a microtiter plate, followed by 2 pt of chromogenic mixture (aromatic alkyl-amine) and 200 μL of acetate buffer, pH 4.8. After gentle mixing, the plate was incubated at 37° C. for 90 min and the optical densities read at λ=540 nm in a microplate reader. Results of the d-ROMS test were expressed according to the following formula: [Sample] (mM $H_2O_2$)=Abs sample/Abs calibrator X [calibrator] (mM $H_2O_2$). The d-ROMS test sensitivity was 0.26 mM and the method was linear up to 267 mM $H_2O_2$. Intra- and inter-assay coefficients of variation were below 5%.

Cytokines Determination

The portion from the heart corresponding to the area at risk was homogenized in (PBS) containing protease inhibitors (Roche Italia, Italy) with a tissue grinder and a disperser-homogenizer. An aliquot of the homogenates was centrifuged at 13,000 rpm for 30 min at 4° C. and the supernatants were used for cytokine analysis. IL-6, IL-1β and TNF-α were determined by LaboSpace (Milan, Italy) using the biomarker multiplex immunoassay that measures multiple proteins in a single sample using mixed microbeads on the Luminex® platform. Determinations were performed in triplicate.

Western Blotting

The abundance of proteins of interest in area at risk homogenates was determined by Western blotting. Briefly, the total proteins were measured in each homogenate using the Coomassie Blue kit (Bio-Rad Laboratories Italia, Italy) according to the manufacturer's instructions, and 50 μg per sample was separated on SDS-PAGE gel and electroblotted onto a nitrocellulose membrane (Bio-Rad Laboratories Italia, Italy). After washing in tris-buffered saline containing 0.1% Tween-20 (TBS-T) and blocking with 5% non-fat dry milk for 1 h at room temperature, membranes were probed overnight at 4° C. with the following primary antibodies: rabbit anti-nuclear factor-erythroid 2-related factor 2 (Nrf2,) (Santa Cruz Biotechnology, USA) dilution 1:500 in TBS-T, anti-HO1 (Abcam) dilution 1:1000 in TBS-T and BSA 1%, anti-SPTLC 1 and anti-SPTLC2 (Abcam) dilution 1:200 in TBS-T and α-tubulin (Santa Cruz Biotechnology, USA) dilution 1:1000 in TBS-T. After three washes in TBS-T, the blot was incubated with a horseradish peroxidase-conjugated anti-rabbit IgG (Pierce, Thermo Fisher Scientific, USA; diluted 1:10,000 in TBS-T) for 1 h at room temperature. After the final washings, the signal was developed using an enhanced chemiluminescent horseradish peroxidase substrate (LiteAblot, Euroclone, Italy), and bands were captured and quantified under a BioRad GelDoc 2000 imager. Band intensity in each lane was normalized by the signal of a loading control (α-tubulin). For each antigen, the quantification was obtained by averaging the results of at least three independent experiments.

Data Analysis

In examples 1-5 below, the animal experiments were performed in triplicate using a minimum of seven animals for each group. All graphs were created using the GraphPad software. Whenever quantitative analyses are reported, data are expressed as mean±SEM calculated from experimental replicates. Data significance was evaluated by one-way ANOVA followed by the Bonferroni posttest when significant ($p<0.05$) or by unpaired t test (significant when $p<0.05$). The images shown for Western blots are the most representative.

In example 7 below data have been obtained as medium values of triplicate measurements per mice, with treatment groups formed by a minimum of seven animals per group. All graphs were created using the GraphPad software. Data are expressed as mean±SEM calculated from experimental replicates. Data significance was evaluated by one-way ANOVA followed by the Bonferroni posttest when significant ($p<0.05$) or by unpaired t test (significant when $p<0.05$).

Echocardiography Fractional Shortening Measurement

Cardiac function was assessed before as well as 24 h or 4 days after the LAD and LAD/Myriocyn administration by transthoracic echocardiography by following the procedure described previously [35]. Animals were anesthetized with isofluorane 5% and the echocardiographic images were obtained during the heart rate stabilized at ~500 beats per minute. Ultrasound scanning was performed by GE Health Care Vision Logic Q Ultrasound System. Using two-dimensional B-mode and M-mode ultrasonography, left ventricle (LV) end-diastolic, end-systolic dimensions (LVEDD and LVESD), anterior and posterior wall thickness and heart rate were measured according to the leading-edge method of the American Society of Echocardiography [36]. LV systolic function represented as fractional shortening (FS) and ejection fraction (EF) were calculated by the equation of FS (%)=[(LVEDD−LVESD)/LVEDD]×100 and EF (%)=Y+[(100−Y)×0.15], where Y=RLVEDD2−LVESD2)/LVEDD21×100 [37].

Example 1—I/R Injury Induces De Novo Synthesis of Ceramide in the Area at Risk

Figure 3:
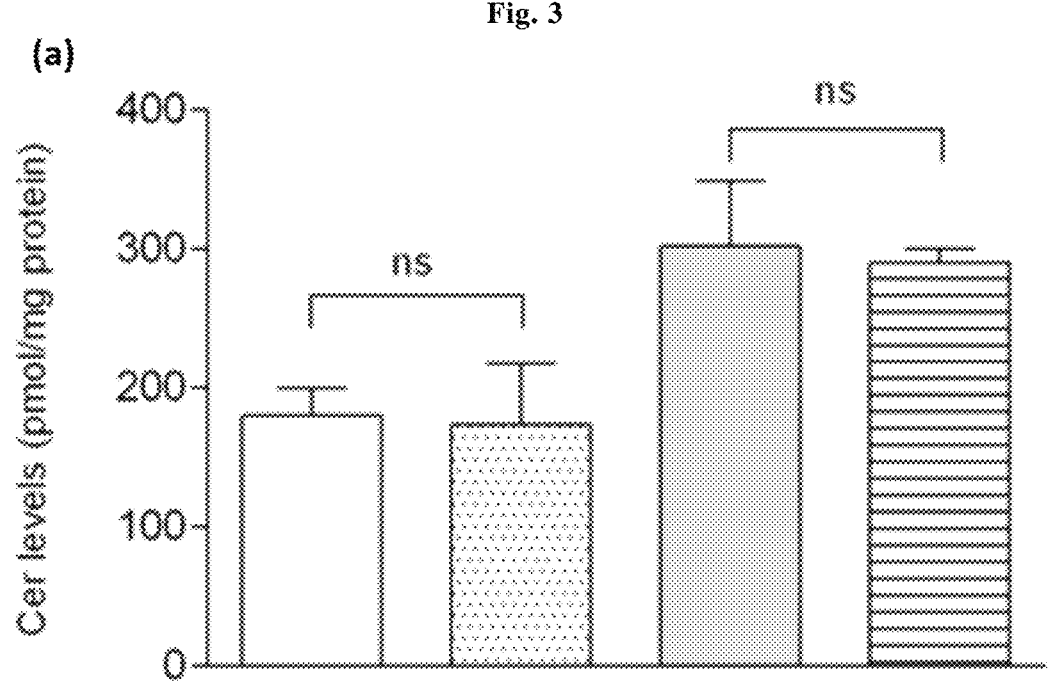
FIG. 3 shows the ceramide tissue levels (a), in at risk and infarct areas percentages (b), and the inflammatory cytokine (IL-β, TNF-α and IL6) mRNA expression levels (c) of sham and I/R treated or not treated with an empty SLN carrier.
Figure 3:
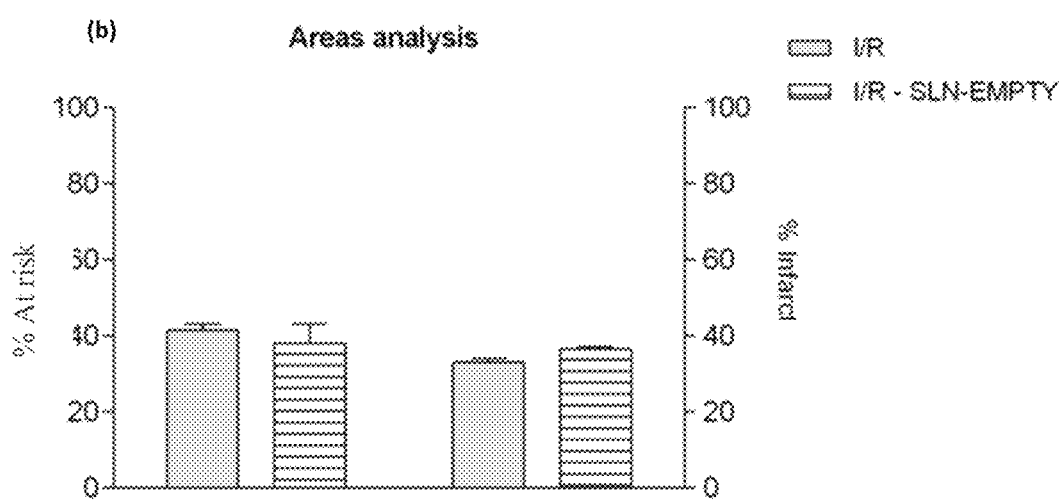
Figure 3:
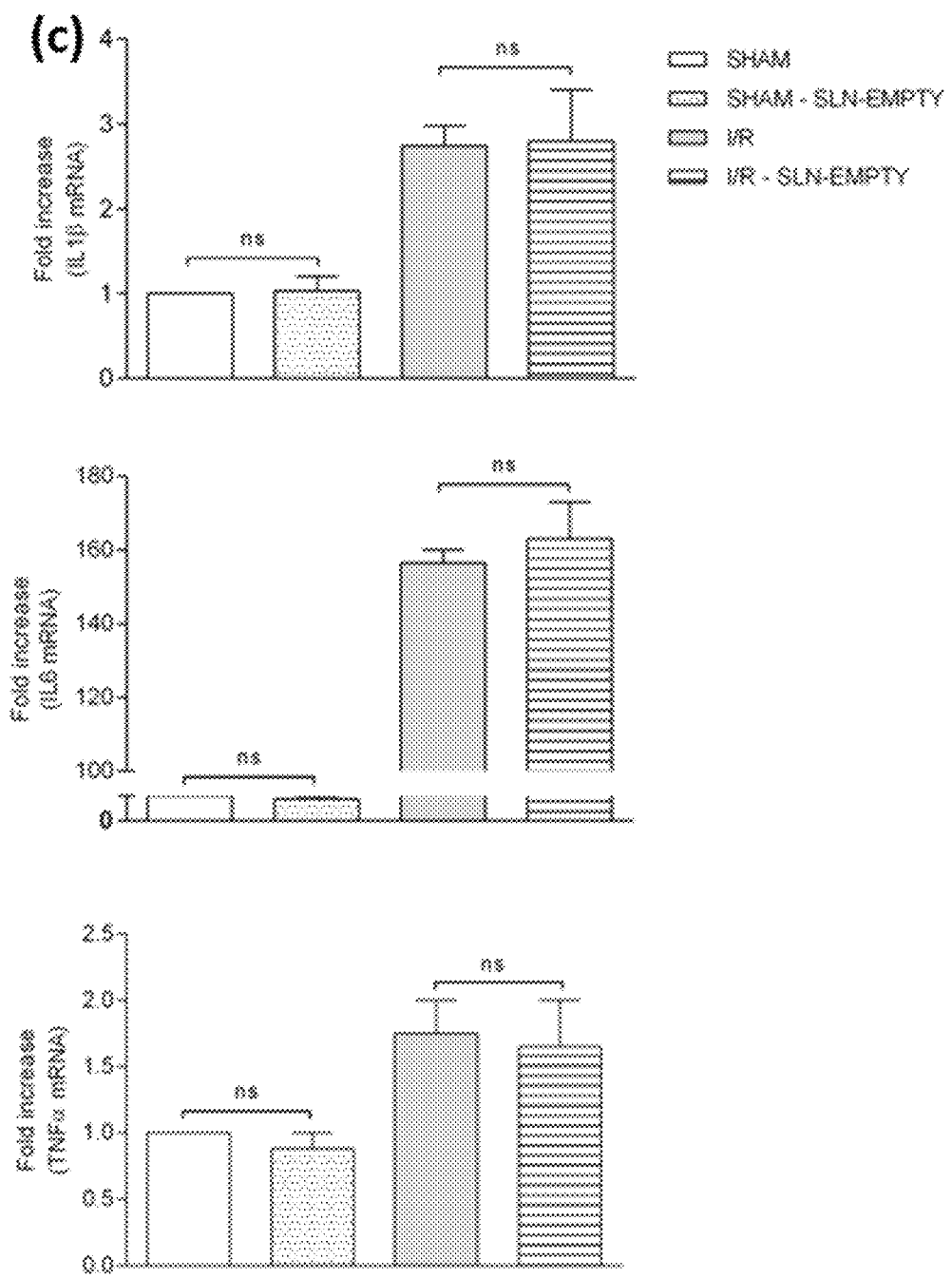
Figure 4:
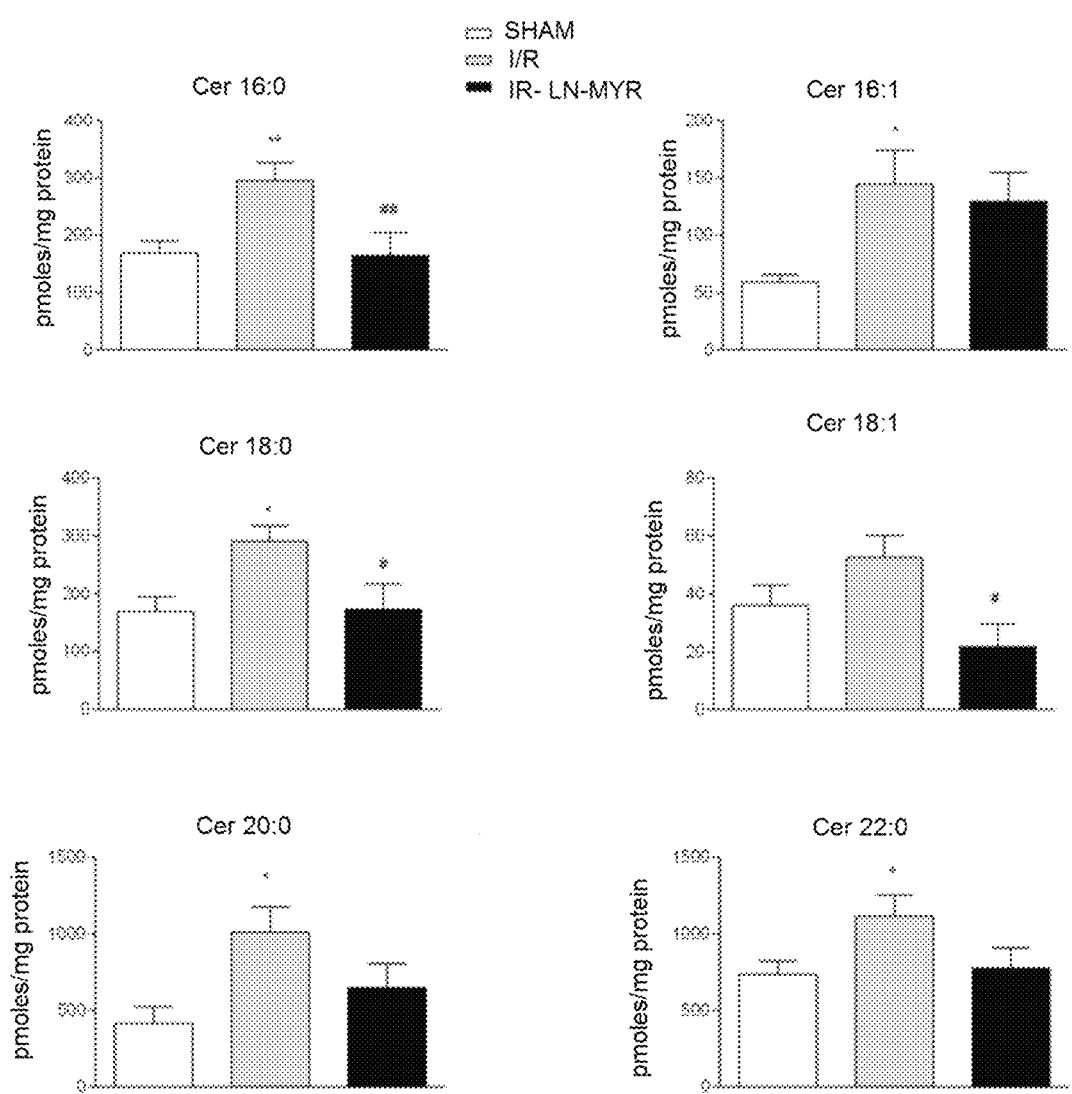
FIG. 4 shows the LCMS quantitation of ceramide species in the at risk area of sham versus I/R mice treated or untreated with SLN-myriocin.
Figure 5:
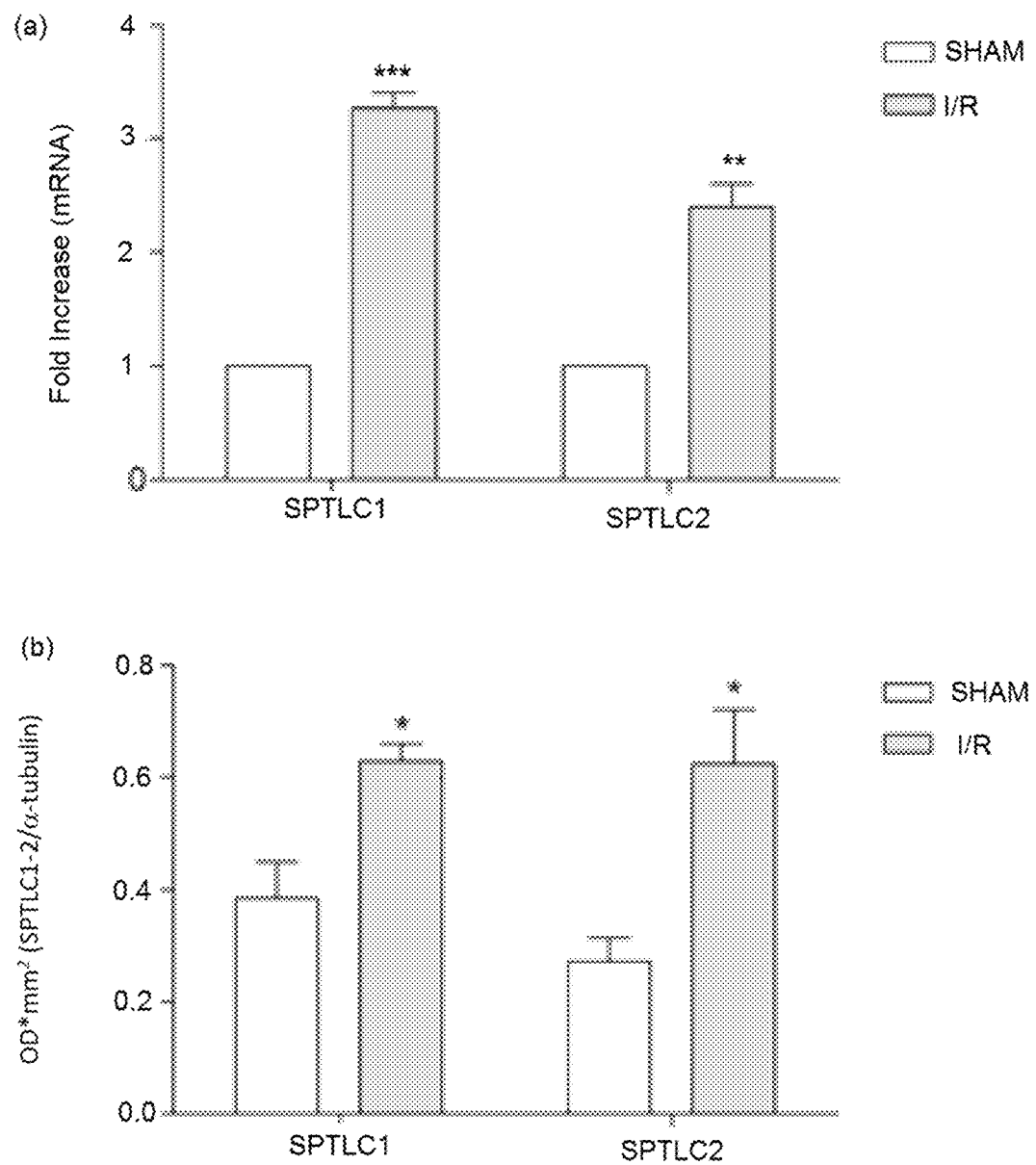
FIG. 5 shows the ceramide de novo synthesis mRNA upregulation in the myocardium at-risk area of I/R vs sham mice, as determined by mRNA quantitation (FIG. 3a), protein expression (FIG. 3b) and western blotting (FIG. 3c).
Figure 5:
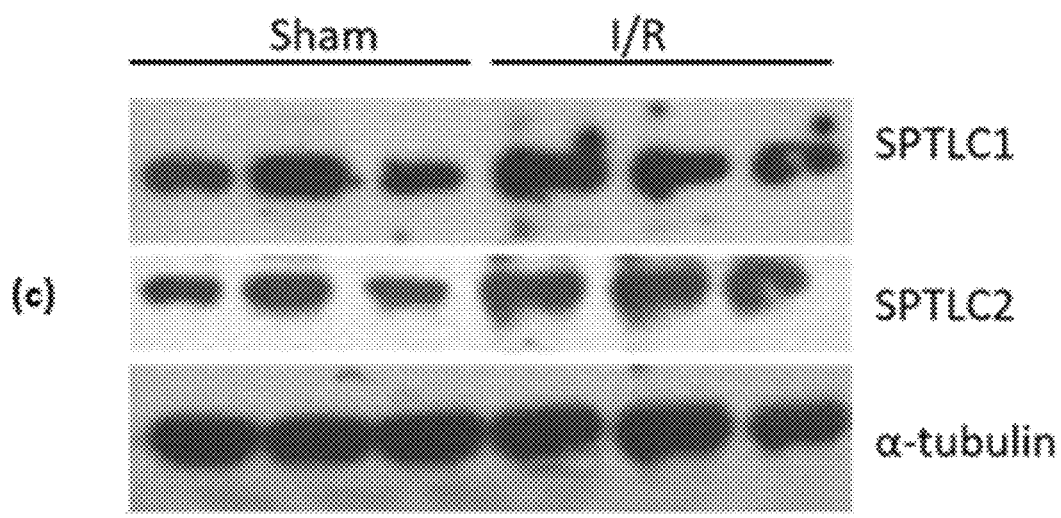

To evaluate variations in myocardial ceramide content during reperfusion injury, we used a murine model of I/R obtained by 20 min LAD coronary ligature occlusion followed by 3 h reperfusion. For this analytic determination, we kept distinct the infarcted area from the area at risk and from the remaining healthy area. The procedure allowed obtaining an area at risk corresponding to 52.1% of the whole heart; from this area at risk, a portion corresponding to 38.9% is the infarct area. We quantified total ceramides in heart homogenates of the three dissected areas, infarcted at risk and healthy, by LCMS (FIG. 1). An approximately 2.4-fold increase in ceramide was found both in the infarct area and in the area at risk, relative to the basal levels measured in the healthy portions of the same samples (3512.5±545.8 pmol ceramides/mg of proteins in infarct; 3838.1±468.4 pmol ceramides/mg of proteins in at-risk areas; versus 1475±236 pmol ceramides/mg of proteins of ceramide in healthy areas). To evaluate ceramide causal role in I/R injury, we treated mice with nanocarriers (SLN) loaded with SPT inhibitor myriocin, administered by intraventricular injection at reperfusion. The treatment more than halved ceramide mass in the area at risk (from 3838.1±468.1 pmol/mg proteins of ceramide in the I/R only, to 2015.1±421.3 pmol/mg proteins of ceramide in the I/R mice treated with SLN-myriocin, amounting to a 1.9-fold reduction in ceramide), while leaving unaltered ceramide levels in the healthy area. That is, in the presence of myriocin at reperfusion, ceramide levels in the area at risk dropped to only 1.2-fold those in the healthy myocardium. Expectedly, no statistically significant variation of ceramide was found by contrast in the infarct area after myriocin treatment (drug diffusion/effect within necrotic tissue is unattainable). The administration of vehicle (empty SLN) did not affect ceramide levels in I/R animals or in sham (FIG. 3a). Ceramides belong to a family of molecules with different acyl chains, reported to produce distinct, though difficult to tell apart, biological effects. The variations that we report above did not affect differentially the various ceramide species, but were evenly distributed across all species; this holds true in particular for the predominant C-16:0, C-18:0 and C-24:0 ceramides (FIG. 4). To confirm that myriocin is countering a pathological mechanism occurring at reperfusion, we evaluated the expression of SPT, the enzyme that is the direct target of myriocin in the area at risk. We observed a significant increase of the two widely expressed subunits SPTLC1 (3.2 fold) and SPTLC2 (2.3 fold) at the transcript level (FIG. 5a), with a concomitant increase of their protein expression (FIG. 5b, c), in the area at risk of I/R in comparison to sham samples. Altogether, the above data strongly suggest that I/R stimulates ceramide accumulation by a transcriptional activation of the de novo synthesis pathway and this effect can be inhibited by myriocin. By contrast, the low homeostatic levels of ceramide in the healthy myocardial tissue can be maintained even if its synthesis is inhibited due to i) the fact that endogenous control of SPT activity via ORM enzymes in physiologic conditions can buffer the myriocin effect [38]; and ii) the observation that SPT activity is pathologically enhanced in infarcted/suffering areas that are therefore majorly sensitive to myriocin action.

Example 2—Ceramide Synthesis Inhibition Reduces Infarct Size

Figure 6:
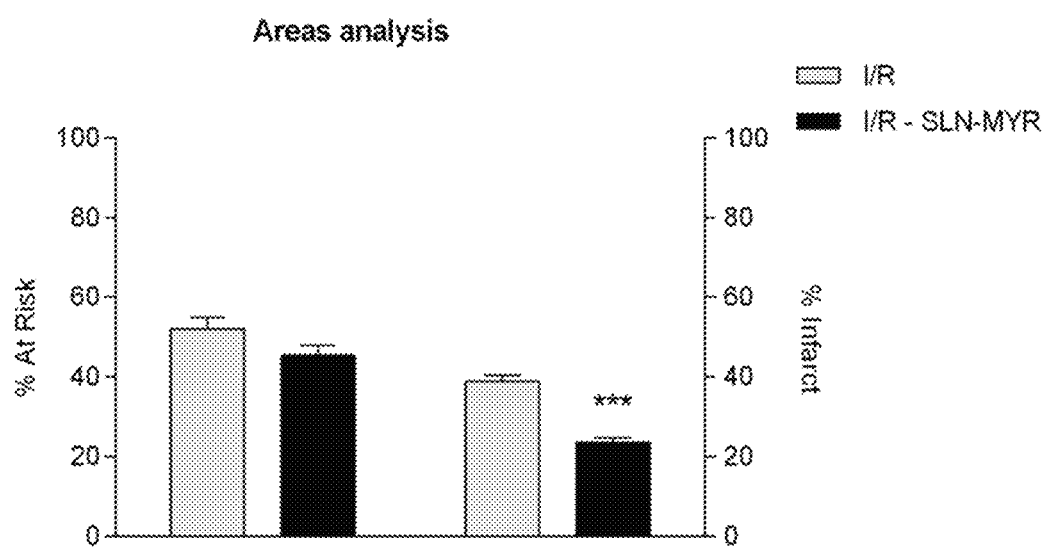
FIG. 6 shows the percentage of at-risk and infarcted areas of I/R mice hearts treated or untreated with SLN-myriocin.

To investigate the potential of inhibiting ceramide synthesis as a strategy to reduce I/R injury, we measured the average infarct areas and the surrounding areas after SLN-myriocin intraventricular treatment at reperfusion. We observed a significant decrease of the infarct size (calculated as percentage of the area at risk), dropping from 38.9%±1.5 in the I/R group to 23.6%±1.1 in the I/R group treated with SLN-myriocin, whereas no significant change was observed in the size of the area at risk, as expected for a consistent LAD ligation procedure (reproducible ischemia dimensions after LAD occlusion across the different groups) (FIG. 6). Both in the I/R and sham, the administration of empty SLN did not affect the infarct size (FIG. 3b).

Following the introduction of the ischemic postconditioning paradigm [39], a number of preclinical studies implementing the same approach have reported reductions of the infarct size falling between 30 and 40% [5, 40-46]: with the upper limit represented by a 50% reduction [53]. Similar figures (ca. 35% reduction [47]) can be found in phase II studies published to date Therefore, protection imparted by myriocin ranks at the high end of the protection range ensured by the benchmark, ischemic postconditioning.

Example 3—Ceramide Synthesis Inhibition Attenuates the Inflammatory Response in the Area at Risk To investigate the role of ceramide in inflammation-induced injury upon I/R, first we determined in the area at risk the mRNA levels for three cytokines primarily involved in the acute inflammatory response: TNF-α, IL1-β and IL-6 [48]). We observed a fold increase of 1.8, 3.2 and 12.3 for TNF-α, IL1-β and IL-6, respectively, in I/R compared to sham. To be noted, higher cytokine expression mirrored the increase of SPTLC1 and SPTLC2 transcripts and the rise of ceramide levels of example 1. SLN-myriocin administration upon reperfusion diminished cytokine production in the area at risk, compared to the untreated I/R group, with a fold decrease of 2.2, 1.7 and 1.3 for TNF-α, IL1-β and IL-6, respectively (FIG. 2a). The same cytokines were also directly assayed as proteins in the homogenates from the area at risk. As expected from their mRNAs, an increase of these proteins was observed in the I/R versus sham samples (11.4±1.2, 517.3±54.1 and 241.9±48.1 pg/mL for TNF-α, IL1-β and IL-6 respectively), while SLN-myriocin treatment decreased the levels to 8.2±0.9, 349.6±51.2 and 219±32.5 pg/mL for TNF-a, IL1-b and IL-6, respectively, relative to the untreated I/R (FIG. 2b). The administration of empty SLN did not affect pro-inflammatory mediator release, both in sham and I/R samples (FIG. 3c).

Example 4—Ceramide Synthesis Inhibition Reduces Myocardial ROS Production

Figure 7:
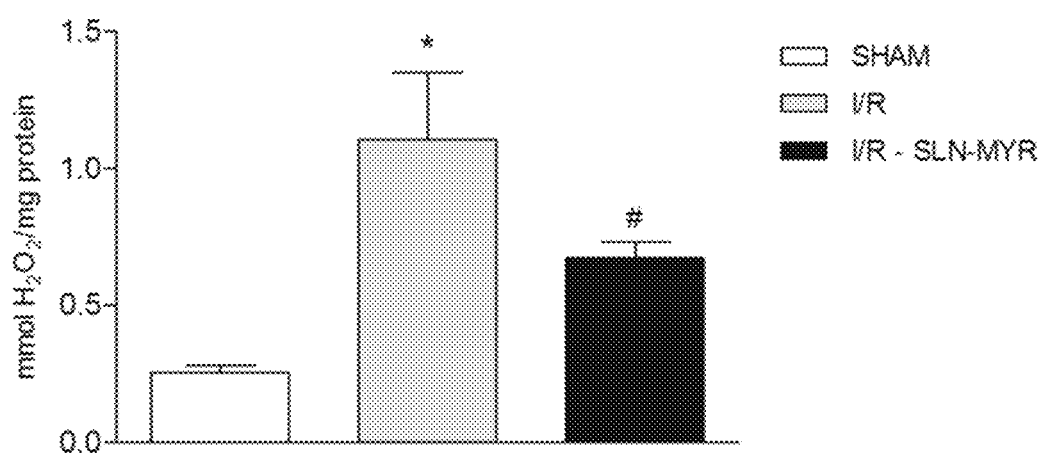
FIG. 7 shows the $H_2O_2$ production in the mycocardial at risk area of sham and I/R mice treated of untreaed with SLN-myriocin.

Since oxidative stress is a key trigger of ischemia-induced inflammation, we evaluated the effect of inhibiting ceramide synthesis on ROS generation in I/R myocardium. We performed the dROMs test on the area-at-risk tissue homogenates, evaluating the concentration of $H_2O_2$ (mmol/L) as an index of ROS production. A heightened ROS concentration was observed in I/R (1.1±0.2 mmol of $H_2O_2$/mg protein) compared to sham (0.2±0.02 mmol of $H_2O_2$/mg protein). SLN-myriocin treatment reduced ROS concentration by about 1.7-fold (FIG. 7).

Figure 8:
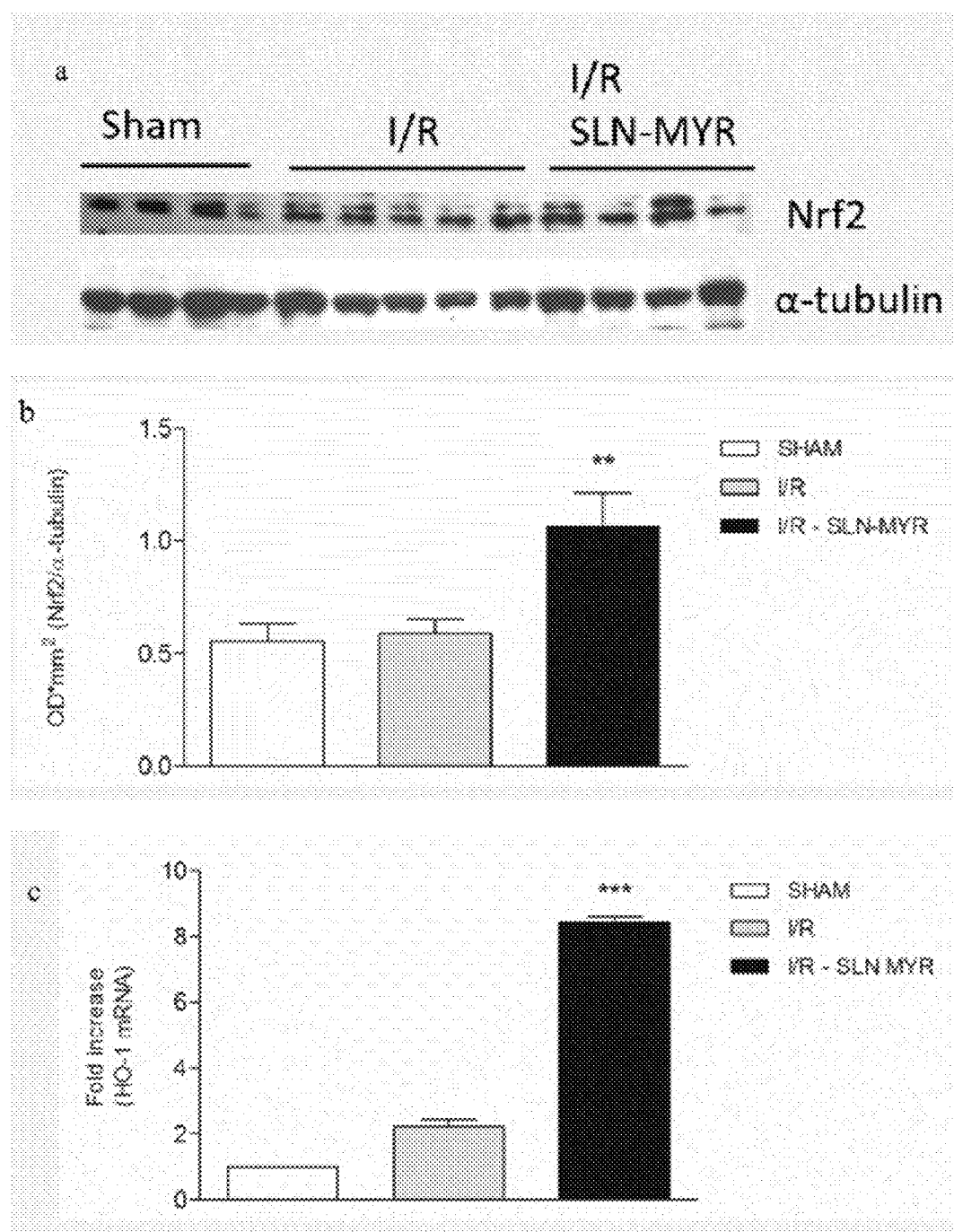
FIG. 8 shows the NrF2 expression in the myocardial at risk area of sham and I/R mice treated or untreated with SLN-myriocin, as determined by western blot (a) and quantitation of the western blot bands (b) and mRNA levels (c).
Figure 9:
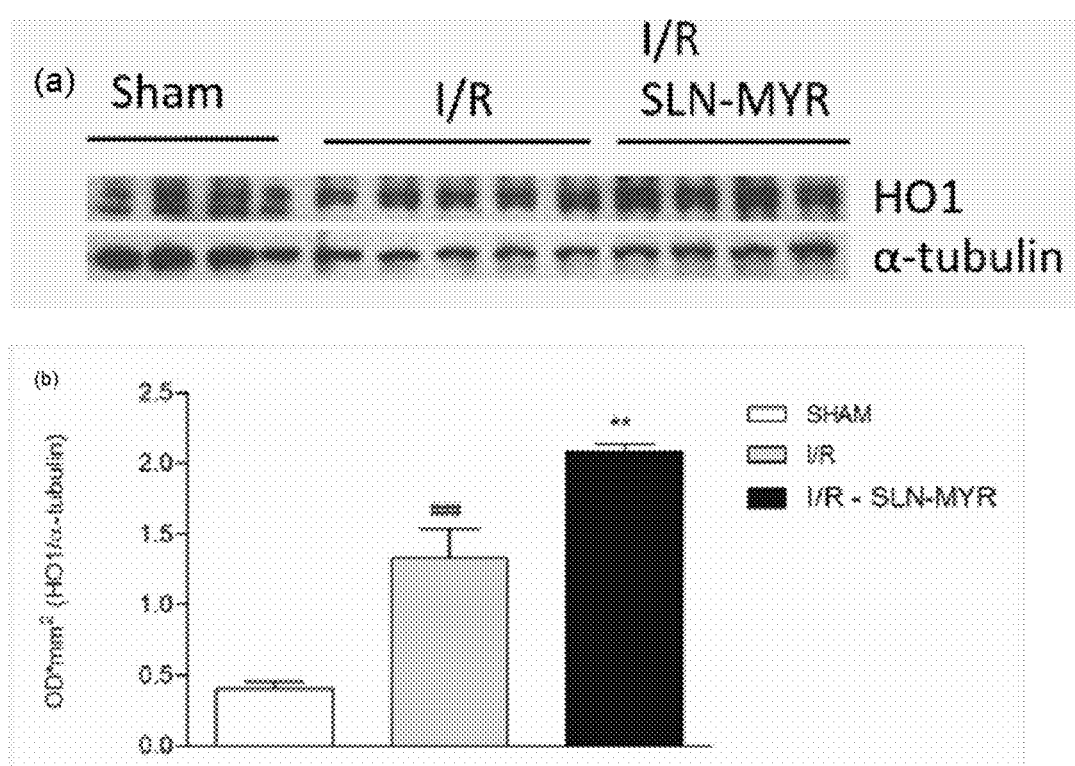
FIG. 9 shows the HO1 expression in the myocardial at risk area of sham and I/R mice treated or untreated with SLN-myriocin, as determined by western blot (a) and quantitation of the western blot bands (b).

Example 5—De Novo Ceramide Synthesis Inhibition Activates Nrf2-HO-1 Pathway Against Oxidative Stress Damage Nrf2 is a transcription factor and cytoprotective response master regulator, which activates cell detoxification and survival program in response to injury and inflammation [49]), by binding to the antioxidant response element (ARE) controlled genes, including genes with a direct antioxidant function such as HO1 [50]. To study if ceramide accumulation contributes to I/R injury by down-modulating the endogenous defensive response against oxidative stress, we evaluated Nrf2 protein levels (FIG. 8a, b) in the area at risk. SLN-myriocin treatment in I/R induced a twofold Nrf2 protein increase over untreated I/R. Furthermore, we observed a fourfold increase in HO1 transcripts (FIG. 8c) and a twofold increase of HO1 protein (FIG. 9d, e) in the area at risk of SLN-myriocin-treated I/R myocardium in comparison to untreated I/R. These results indicate that ceramide de novo synthesis inhibition restores defensive and survival mechanisms that are impaired upon ceramide accumulation.

This myriocin-induced activation of the Nrf2-HO1 pathway, in resemblance of hypoxia preconditioning, is expected to exert a cardioprotective action against I/R-induced oxidative stress, an indirect and powerful anti-inflammatory effect [51], as well as to protect against ventricular arrhythmias by attenuating NGF-induced sympathetic innervation [52].

Example 6—Myoricin Activity in Reperfusion Injury

Figure 10:
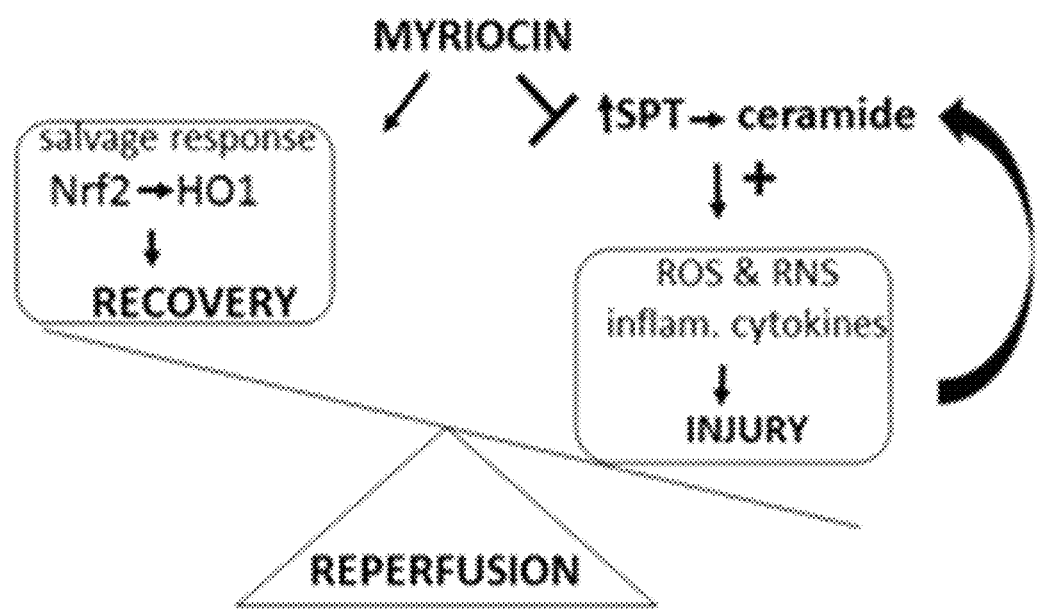
FIG. 10 shows a schematic representation of SPT, ceramide and myriocin effects on I/R injury as a seesaw diagram.

FIG. 10 recapitulates the main findings of the invention and shows how Myoricin surprisingly acts both by minimizing injury through the inhibition of the vicious circle of of ceramide production and by stimulating recovery through the Nrf2-HO1pathway.

Example 7—De Novo Ceramide Synthesis Inhibition Improves Cardiac Contractility

Figure 11:
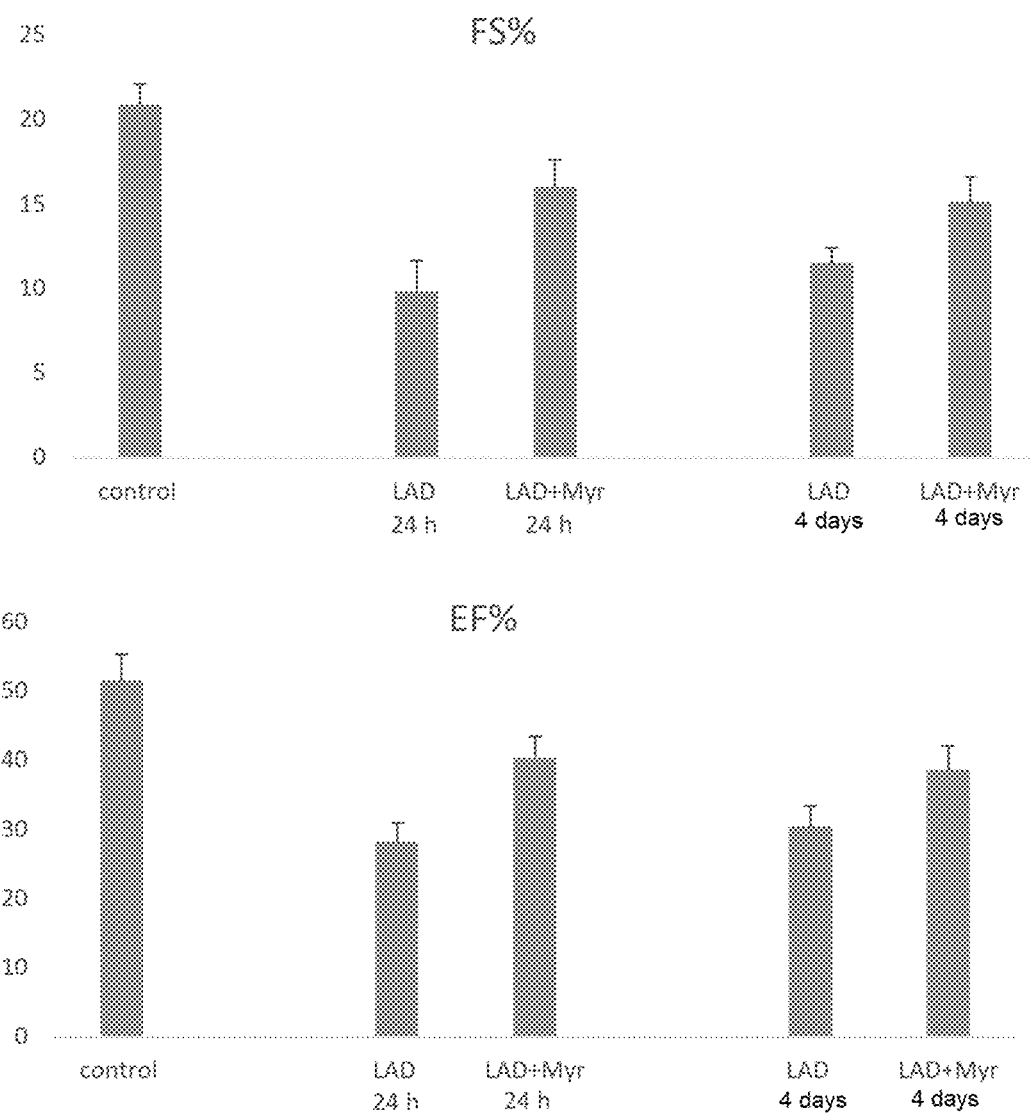
FIG. 11 shows the Echography Fractional Shortening measurements of sham and I/R mice treated or untreated with SLN-myriocin, after 24 hours or 4 days of reperfusion.

To evaluate the effect on cardiac contractility of treatment with a de novo ceramide synthesis inhibitor, we measured the contractility by Fractional Shortening (FS %) and the functionality by Ejection Fraction (EF %) of control and I/R mice treated or untreated with SLN-myriocin (FIG. 11). As expected, LAD reduced FS by 45% (FS: control 20, 9%±1.2; LAD 11.5%±0.9;) and EF by 41% (ES: control 51.6%±3.8 LAD 30.4%±2.9), measured at days after infarct. This reduction is significantly contrasted by myriocin post-conditioning, and FS reduction lowered to 27.6% (FS, LAD+ Myr 15.1%±1.5) whereas EF reduction lowered to 25% (EF, LAD+MYR 38.6%±3.5). Approximately we can conclude that myriocin post-conditioning reduced contractility and functional damage, visualized by ultrasound echocardial analysis, by 40%.

BIBLIOGRAPHY

1. Lonborg J T (2015) Targeting reperfusion injury in the era of primary percutaneous coronary intervention: hope or hype? Heart. doi:10.1136/heartjn1-2015-307804.
2. Mezzaroma E, Toldo S, Farkas D, Seropian I M, Van Tassell B W, Salloum F N, Kannan H R, Menna A C, Voelkel N F, Abbate A (2011) The inflammasome promotes adverse cardiac remodelling following acute myocardial infarction in the mouse. Proc Natl Acad Sci USA 108:19725-19730. doi:10.1073/pnas.1108586108.
3. Collard C D, Gelman S (2001) Pathophysiology, clinical manifestations, and prevention of ischemia-reperfusion injury. Anesthesiology 94:1133-1138.
4. Romson J L, Hook B G, Kunkel S L, Abrams G D, Schork M A, Lucchesi B R (1983) Reduction of the extent of ischemic myocardial injury by neutrophil depletion in the dog. Circulation 67:1016-1023.

5. Heusch G (2013) Cardioprotection: chances and challenges of its translation to the clinic. Lancet 381:166-175. doi:10.1016/S0140-6736(12)60916-7.
6. Heusch G (2015) Molecular basis of cardioprotection: signal transduction in ischemic pre-, post-, and remote conditioning. Circ Res 116:674-699. doi:10.1161/CIRCRESAHA.116.305348.
7. Ibanez B, Heusch G, Ovize M, Van de Werf F (2015) Evolving therapies for myocardial ischemia/reperfusion injury. J Am Coll Cardiol 65:1454-1471. doi: 10.1016/j.jacc.2015.02.032.
8. Kleinbongard P, Heusch G (2015) Extracellular signalling molecules in the ischaemic/reperfused heart—druggable and translatable for cardioprotection? Br J Pharmacol 172:2010-2025. doi:10.1111/bph.12902.
9. El Messaoudi S, Schreuder T H, Kengen R D, Rongen G A, van den Broek P H, Thijssen D H, Riksen N P (2014) Impact of metformin on endothelial ischemia-reperfusion injury in humans in vivo: a prospective randomized open, blinded-endpoint study. PLoS One 9:e96062. doi: 10.1371/journal.pone.0096062.
10. Opfermann P, Derhaschnig U, Felli A, Wenisch J, Santer D, Zuckermann A, Dworschak M, Jilma B, Steinlechner B (2015) A pilot study on reparixin, a CXCR1/2 antagonist, to assess safety and efficacy in attenuating ischaemia-reperfusion injury and inflammation after on-pump coronary artery bypass graft surgery. Clin Exp Immunol 180:131-142. doi:10.1111/cei.12488.
11. Targeting fatty acid and carbohydrate oxidation—a novel therapeutic intervention in the ischemic and failing heart. Jaswal J S, Keung W, Wang W, Ussher J R, Lopaschuk G D. Biochim Biophys Acta. 2011 July; 1813(7):1333-50. doi: 10.1016/j.bbamcr.2011.01.015. Review.PMID: 21256164).
12. Bartke N, Hannun Y A (2009) Bioactive sphingolipids: metabolism and function. J Lipid Res 50(Suppl):S91-S96. doi:10.1194/jlr.R800080-JLR200.
13. Sphingolipid metabolism and neutral sphingomyelinases. Airola M V, Hannun Y A. Handb Exp Pharmacol. 2013; (215):57-76. doi: 10.1007/978-3-7091-1368-4_3.
14. Gulbins E, Kolesnick R (2003) Raft ceramide in molecular medicine. Oncogene 22:7070-7077. doi:10.1038/sj.onc.1207146.
15. Medler T R, Petrusca D N, Lee P J, Hubbard W C, Berdyshev E V, Skirball J, Kamocki K, Schuchman E, Tuder R M, Petrache I (2008) Apoptotic sphingolipid signaling by ceramides in lung endothelial cells. Am J Respir Cell Mol Biol 38:639-646. doi:10.1165/rcmb.2007-02740C.
16. Gomez L, Paillard M, Price M, Chen Q, Teixeira G, Spiegel S, Lesnefsky E J (2011) A novel role for mitochondrial sphingosine 1-phosphate produced by sphingosine kinase-2 in PTP-mediated cell survival during cardioprotection Basic Res Cardiol 106:1341-1353. doi: 10.1007/s00395-011-0223-7.
17. Zhang D X, Fryer R M, Hsu A K, Zou A P, Gross G J, Campbell W B, Li P L (2001) Production and metabolism of ceramide in normal and ischemic-reperfused myocardium of rats. Basic Res Cardiol 96:267-274.
18. Cordis G A, Yoshida T, Das D K (1998) HPTLC analysis of sphingomyelin, ceramide and sphingosine in ischemic/reperfused rat heart. J Pharm Biomed Anal 16:1189-1193.
19. Cui J, Engelman R M, Maulik N, Das D K (2004) Role of ceramide in ischemic preconditioning. J Am Coll Surg 198:770-777. doi:10.1016/j.jamcollsurg.2003.12.016.
20. Drevinge C, Karlsson L O, Stahlman M, Larsson T, Perman Sundelin J, Grip L, Andersson L, Boren J, Levin M C (2013) Cholesteryl esters accumulate in the heart in a porcine model of ischemia and reperfusion. PLoS One 8:e61942. doi:10.1371/journal.pone.0061942.
21. Empinado H M, Deevska G M, Nikolova-Karakashian M, Yoo J K, Christou D D, Ferreira L F (2014) Diaphragm dysfunction in heart failure is accompanied by increases in neutral sphingomyelinase activity and ceramide content. Eur J Heart Fai 16:519-525. doi:10.1002/ejhf.73.
22. Cell Physiol Biochem. 2010; 26(1):9-20. doi: 10.1159/000315101. Functional Inhibitors of Acid Sphingomyelinase (FIASMAs): a novel pharmacological group of drugs with broad clinical applications. Kornhuber J, Tripal P, Reichel M, Mühle C, Rhein C, Muehlbacher M, Groemer T W, Gulbins E.
23. Usta E, Mustafi M, Artunc F, Walker T, Voth V, Aebert H, Ziemer G (2011) The challenge to verify ceramide's role of apoptosis induction in human cardiomyocytes—a pilot study. J Cardiothorac Surg 6:38. doi:10.1186/1749-8090-6-38.
24. Cuzzocrea S, Di Paola R, Genovese T, Mazzon E, Esposito E, Crisafulli C, Bramanti P, Salvemini D (2008) Anti-inflammatory and anti-apoptotic effects of fumonisin B1, an inhibitor of ceramide synthase, in a rodent model of splanchnic ischemia and reperfusion injury. J Pharmacol Exp Ther 327:45-57. doi:10.1124/jpet.108.139808.
25. Desipramine for neuropathic pain in adults. Hearn L, Moore R A, Derry S, Wiffen P J, Phillips T. Cochrane Database Syst Rev. 2014 Sep. 23; (9):CD011003. doi: 10.1002/14651858.CD011003.pub2. Review.PMID: 25246131.
26. In vivo toxicity studies of fusarium mycotoxins in the last decade: a review. Escrivá L, Font G, Manyes L. Food Chem Toxicol. 2015 April; 78:185-206. doi: 10.1016/j.fct.2015.02.005. Review.PMID:25680507.
27. Park T S, Hu Y, Noh H L, Drosatos K, Okajima K, Buchanan J, Tuinei J, Homma S, Jiang X C, Abel E D, Goldberg I J (2008) Ceramide is a cardiotoxin in lipotoxic cardiomyopathy. J Lipid Res 49:2101-2112. doi:10.1194/jlr.M800147-JLR200.
28. J Am Chem Soc. 2013 Sep. 25; 135(38):14276-85. doi: 10.1021/ja4059876. Epub 2013 Sep. 11. The chemical basis of serine palmitoyltransferase inhibition by myriocin. Wadsworth J M1, Clarke D J, McMahon S A, Lowther J P, Beattie A E, Langridge-Smith P R, Broughton H B, Dunn T M, Naismith J H, Campopiano D J.
29. Strettoi E, Gargini C, Novelli E, Sala G, Piano I, Gasco P, Ghidoni R (2010) Inhibition of ceramide biosynthesis preserves photoreceptor structure and function in a mouse model of retinitis pigmentosa. Proc Natl Acad Sci USA 107:18706-18711. doi:10.1073/pnas.1007644107.
30. Caretti A, Bragonzi A, Facchini M, De Fino I, Riva C, Gasco P, Musicanti C, Casas J, Fabrias G, Ghidoni R, Signorelli P (2014) Anti-inflammatory action of lipid nanocarrier-delivered myriocin: therapeutic potential in cystic fibrosis. Biochim Biophys Acta 1840:586-594. doi: 10.1016/j.bbagen.2013.10.018.
31. Hodson et al. Cardiovasc Diabetol (2015) 14:153 DOI 10.1186/s12933-015-0316-y.
32. Ussher et al., PLoS One. 2012; 7(5):e37703. doi: 10.1371/journal.pone.0037703.
33. Chun et al., Diabetes Res Clin Pract. 2011 July; 93(1): 77-85. doi: 10.1016/j.diabres.2011.03.017.
34. Munoz-Olaya J M, Matabosch X, Bedia C, Egido-Gabas M, Casas J, Llebaria A, Delgado A, Fabrias G (2008) Synthesis and biological activity of a novel inhibitor of dihydroceramide desaturase. ChemMedChem 3:946-953. doi:10.1002/cmdc.200700325.

35. Front Physiol. 2016 Aug. 5; 7:334. doi: 10.3389/fphys.2016.00334. eCollection 2016. S100A8 and S100A9 Are Associated with Doxorubicin-Induced Cardiotoxicity in the Heart of Diabetic Mice. Pei X M1, Tam B T, Sin T K, Wang F F, Yung B Y, Chan L W, Wong C S, Ying M, Lai C W, Siu P M.
36. Lang, R. M., Bierig, M., Devereux, R. B., Flachskampf, F. A., Foster, E., Pellikka, P. A., et al. (2006). Recommendations for chamber quantification. Eur. J. Echocardiogr. 7, 79-108. doi: 0.1016/j.euje.2005.12.014.
37. Dittoe, N., Stultz, D., Schwartz, B. P., and Hahn, H. S. (2007). Quantitative left ventricular systolic function: from chamber to myocardium. Crit. Care Med. 35, S330-5339. doi: 10.1097/01.CCM.0000270245.70103.7E.
38. ORMDL/serine palmitoyltransferase stoichiometry determines effects of ORMDL3 expression on sphingolipid biosynthesis. Siow D, Sunkara M, Dunn T M, Morris A J, Wattenberg B. J Lipid Res. 2015 April; 56(4): 898-908. doi: 10.1194/jlr.M057539.PMID:25691431.
39. Zhao Z Q, Corvera J S, Halkos M E, Kerendi F, Wang N P, Guyton R A, Vinten-Johansen J (2003) Inhibition of myocardial injury by ischemic postconditioning during reperfusion: comparison with ischemic preconditioning. Am J Physiol Heart Circ Physiol 285:H579-H588. doi: 10.1152/ajpheart.01064.2002.
40. Argaud L, Gateau-Roesch O, Raisky O, Loufouat J, Robert D, Ovize M (2005) Postconditioning inhibits mitochondrial permeability transition. Circulation 111: 194-197. doi:10.1161/01.CIR.0000151290.04952.3B.
41. Darling C E, Jiang R, Maynard M, Whittaker P, Vinten-Johansen J, Przyklenk K (2005) Postconditioning via stuttering reperfusion limits myocardial infarct size in rabbit hearts: role of ERK1/2. Am J Physiol Heart Circ Physiol 289:H1618-H1626. doi:10.1152/ajpheart.00055.2005.
42. Schwartz L M, Lagranha C J (2006) Ischemic postconditioning during reperfusion activates Akt and ERK without protecting against lethal myocardial ischemia-reperfusion injury in pigs. Am J Physiol Heart Circ Physiol 290:H1011-H1018. doi:10.1152/ajpheart.00864.2005.
43. Skyschally A, van Caster P, Iliodromitis E K, Schulz R, Kremastinos D T, Heusch G (2009) Ischemic postconditioning: experimental models and protocol algorithms Basic Res Cardiol 104:469-483. doi:10.1007/s00395-009-0040-4.
44. Tang X L, Sato H, Tiwari S, Dawn B, Bi Q, Li Q, Shirk G, Bolli R (2006) Cardioprotection by postconditioning in conscious rats is limited to coronary occlusions\45 min Am J Physiol Heart Circ Physiol 291:H2308-H2317. doi:10.1152/ajpheart.00479.2006.
45. Tsang A, Hausenloy D J, Mocanu M M, Yellon D M (2004) Postconditioning: a form of "modified reperfusion" protects the myocardium by activating the phosphatidylinositol 3-kinase-Akt pathway. Circ Res 95:230-232. doi:10.1161/01.RES.0000138303.76488.fe.
46. Yang X M, Proctor J B, Cui L, Krieg T, Downey J M, Cohen M V (2004) Multiple, brief coronary occlusions during early reperfusion protect rabbit hearts by targeting cell signaling pathways. J Am Coll Cardiol 44:1103-1110. doi:10.1016/j.jacc.2004.05.060.
47. Ovize M, Thibault H, Przyklenk K (2013) Myocardial conditioning: opportunities for clinical translation. Cardiovasc Res 113:439-450. doi:10.1161/CIRCRESAHA.113.300764.
48. Herskowitz A, Choi S, Ansari A A, Wesselingh S (1995) Cytokine mRNA expression in postischemic/reperfused myocardium. Am J Pathol 146:419-428.
49. Calvert J W, Jha S, Gundewar S, Elrod J W, Ramachandran A, Pattillo C B, Kevil C G, Lefer D J (2009) Hydrogen sulfide mediates cardioprotection through Nrf2 signaling. Circ Res 105:365-374. doi:10.1161/CIRCRESAHA.109.199919.
50. Balogun E, Hoque M, Gong P, Killeen E, Green C J, Foresti R, Alam J, Motterlini R (2003) Curcumin activates the haem oxygenase-1 gene via regulation of Nrf2 and the antioxidant-responsive element. Biochem J 371:887-895. doi:10.1042/BJ20021619.
51. Hua W, Chen Q, Gong F, Xie C, Zhou S, Gao L (2013) Cardioprotection of H2S by downregulating iNOS and upregulating HO-1 expression in mice with CVB3-induced myocarditis. Life Sci 93:949-954. doi:10.1016/j.lfs.2013.10.007.
52. Lee T M, Lin S Z, Chang N C (2014) Antiarrhythmic effect of lithium in rats after myocardial infarction by activation of Nrf2/HO-1 signaling. Free Radic Biol Med 77:71-81. doi: 10.1016/j.freeradbiomed.2014.08.022.
53. Yellon D M, Hausenloy D J (2007) Myocardial reperfusion injury. N Engl J Med 357:1121-1135. doi:10.1056/NEJMra071667.

The invention claimed is:

1. A method to treat cardiac reperfusion injury in a mammal, comprising administering to such mammal a composition comprising an inhibitor of the de novo ceramide synthesis pathway, wherein said inhibitor is an inhibitor of serine palmitoyl transferase and wherein said inhibitor is myriocin, stereoisomers, or mixtures of stereoisomers thereof and their pharmaceutically acceptable salts.

2. The method of claim 1, wherein the inhibitor is conjugated to a drug carrier.

3. The method of claim 2, wherein the drug carrier is a nanocarrier.

4. The method of claim 3, wherein the nanocarrier is a lipidic nanocarrier.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Mus musculus

<400> SEQUENCE: 1
agtggtggga gagtcccttt                                              20

<210> SEQ ID NO 2
<211> LENGTH: 20
<212> TYPE: DNA
<213> ORGANISM: Mus musculus

<400> SEQUENCE: 2
cagtgaccac aaccctgatg                                              20
```

```
<210> SEQ ID NO 3
<211> LENGTH: 20
<212> TYPE: DNA
<213> ORGANISM: Mus musculus

<400> SEQUENCE: 3
cctgtcagca gctcatacca                                                   20

<210> SEQ ID NO 4
<211> LENGTH: 20
<212> TYPE: DNA
<213> ORGANISM: Mus musculus

<400> SEQUENCE: 4
cacactgtcc tgggaggaat                                                   20

<210> SEQ ID NO 5
<211> LENGTH: 20
<212> TYPE: DNA
<213> ORGANISM: Mus musculus

<400> SEQUENCE: 5
ccaccacgct cttctgtcta                                                   20

<210> SEQ ID NO 6
<211> LENGTH: 20
<212> TYPE: DNA
<213> ORGANISM: Mus musculus

<400> SEQUENCE: 6
ctgatgagag ggaggccatt                                                   20

<210> SEQ ID NO 7
<211> LENGTH: 20
<212> TYPE: DNA
<213> ORGANISM: Mus musculus

<400> SEQUENCE: 7
aagaagagcc catcctctgt                                                   20

<210> SEQ ID NO 8
<211> LENGTH: 21
<212> TYPE: DNA
<213> ORGANISM: Mus musculus

<400> SEQUENCE: 8
ctaatgggaa cgtcacacac c                                                 21

<210> SEQ ID NO 9
<211> LENGTH: 21
<212> TYPE: DNA
<213> ORGANISM: Mus musculus

<400> SEQUENCE: 9
tgttctctgg gaaatcgtgg a                                                 21

<210> SEQ ID NO 10
<211> LENGTH: 20
<212> TYPE: DNA
<213> ORGANISM: Mus musculus

<400> SEQUENCE: 10
tgcaagtgca tcatcgttgt                                                   20
```

```
<210> SEQ ID NO 11
<211> LENGTH: 20
<212> TYPE: DNA
<213> ORGANISM: Mus musculus

<400> SEQUENCE: 11
tctatcgtgc tcgcatgaac                                              20

<210> SEQ ID NO 12
<211> LENGTH: 20
<212> TYPE: DNA
<213> ORGANISM: Mus musculus

<400> SEQUENCE: 12
ctgtctgtga gggactctgg                                              20

<210> SEQ ID NO 13
<211> LENGTH: 20
<212> TYPE: DNA
<213> ORGANISM: Mus musculus

<400> SEQUENCE: 13
aactttggca ttgtggaagg                                              20

<210> SEQ ID NO 14
<211> LENGTH: 20
<212> TYPE: DNA
<213> ORGANISM: Mus musculus

<400> SEQUENCE: 14
acacattggg ggtaggaaca                                              20
```